United States Patent [19]

Thompson et al.

[11] Patent Number: 4,556,063
[45] Date of Patent: Dec. 3, 1985

[54] TELEMETRY SYSTEM FOR A MEDICAL DEVICE

[75] Inventors: David L. Thompson, Fridley; Robert M. Bennett, Ham Lake; Glenn M. Roline, Anoka, all of Minn.

[73] Assignee: Medtronic, Inc., Minneapolis, Minn.

[21] Appl. No.: 679,152

[22] Filed: Dec. 7, 1984

Related U.S. Application Data

[63] Continuation of Ser. No. 418,925, Sep. 16, 1982, abandoned, which is a continuation of Ser. No. 194,807, Oct. 7, 1980, abandoned.

[51] Int. Cl.⁴ .............................................. A61N 1/00
[52] U.S. Cl. ............................... 128/419 PT; 128/903
[58] Field of Search ................. 128/419 PG, 419 PT, 128/696, 903, 904

[56] References Cited

U.S. PATENT DOCUMENTS

| | | | |
|---|---|---|---|
| 3,199,508 | 8/1965 | Roth | 128/904 |
| 3,453,546 | 7/1969 | Fryer | 128/903 |
| 3,631,860 | 1/1972 | Lopin | 128/419 PG |
| 3,872,252 | 3/1975 | Malchman et al. | 128/419 PT |
| 4,026,305 | 5/1977 | Brownlee et al. | 128/419 PT |
| 4,223,679 | 9/1980 | Schulman et al. | 128/419 PT |
| 4,281,664 | 8/1981 | Duggan | 128/903 |

Primary Examiner—William E. Kamm
Attorney, Agent, or Firm—Robert C. Beck; John L. Rooney; Joseph F. Breimayer

[57] ABSTRACT

A data telemetry system for use with implanted medical devices for transmitting digital and analog data to a remote receiver by enabling different combinations of fixed and variable value current sources according to a telemetry logic code to energize a tank coil and produce a ringing type of variable frequency RF signal.

1 Claim, 4 Drawing Figures

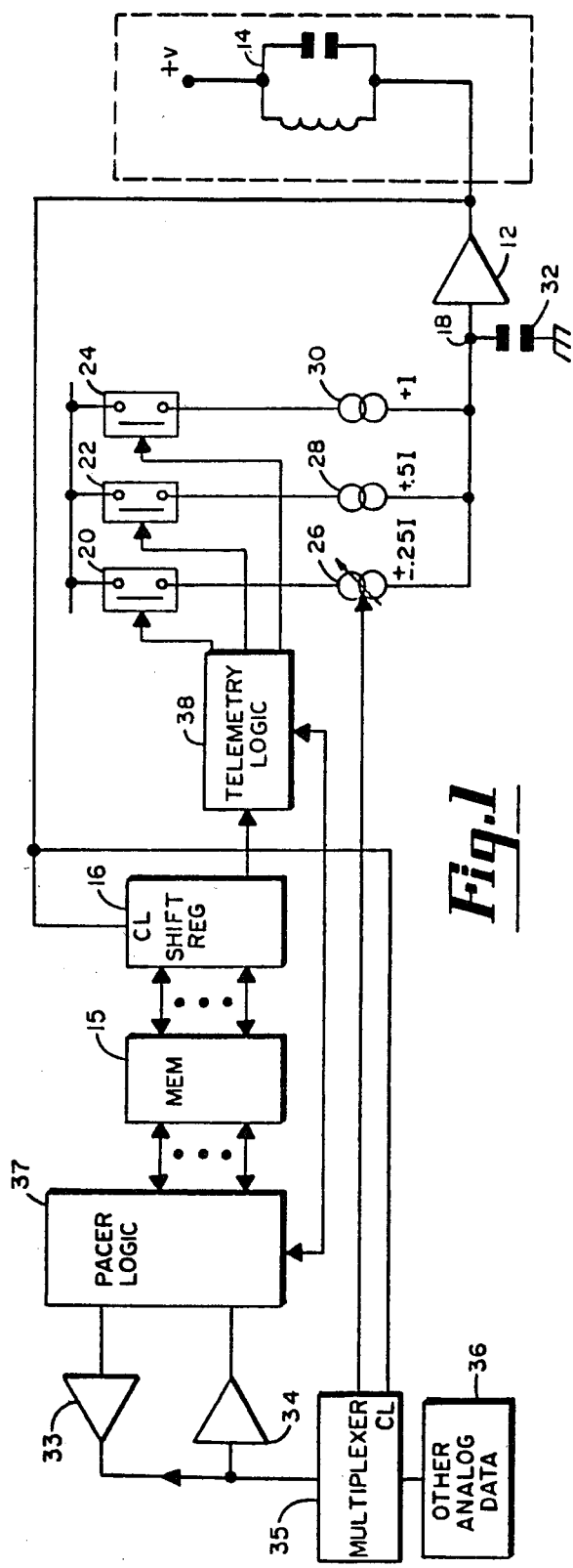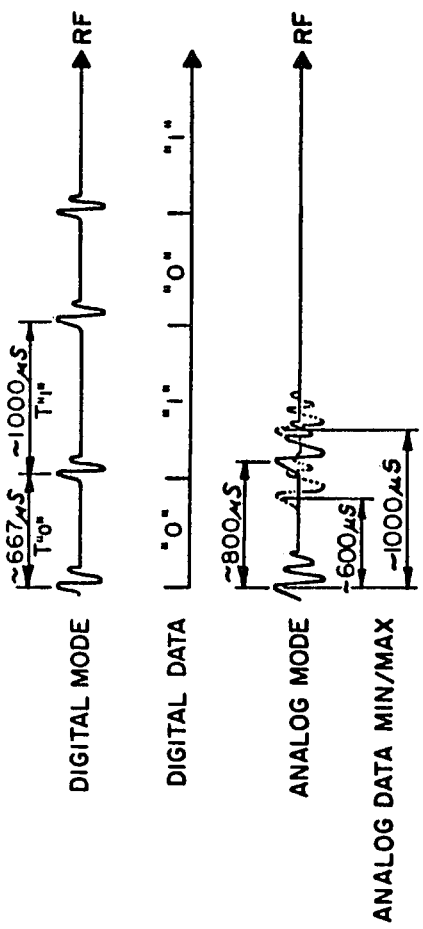

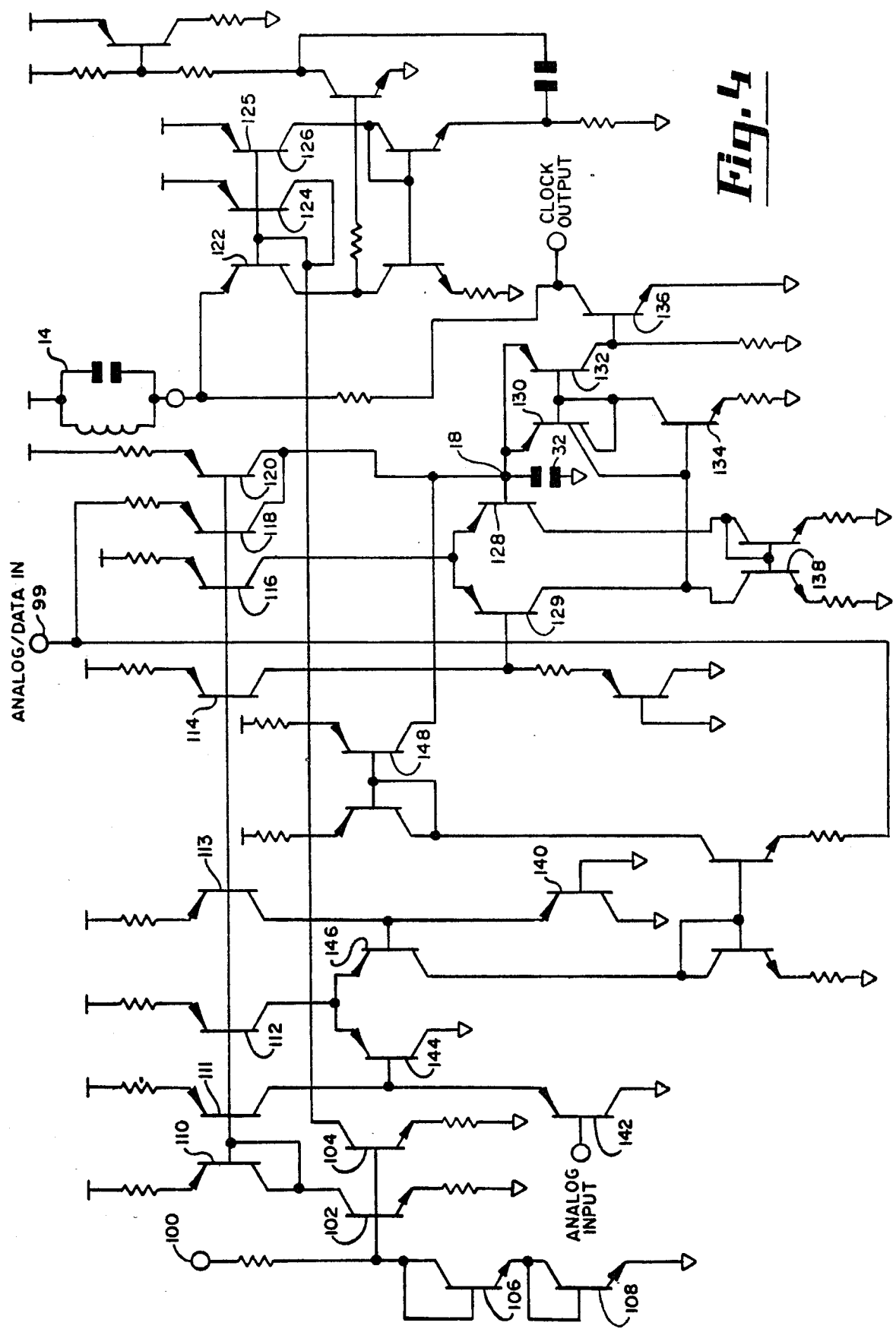

TELEMETRY SYSTEM FOR A MEDICAL DEVICE

This application is a continuation application of Ser. No. 418,925 filed Sept. 16, 1982, now abandoned, which is a continuation of Ser. No. 194,807 filed Oct. 7, 1980, now abandoned.

BACKGROUND OF THE INVENTION

1. Field of the Invention

This invention relates to implantable medical devices such as pacemakers, and more particularly, to a telemetry system for transmitting information from the pacemaker to a remote receiver for diagnostic purposes.

2. Description of the Prior Art

Pacemakers for providing stimulating pulses to the heart in the absence of natural cardiac activity are well-known. Originally, such pacemakers were fabricated from discrete analog components. More recently designed pacemakers employ digital circuitry realized in monolithic form. The additional complexity resulting from monolithic digital implementation has been used to provided desirable pacemaker features, including programmability. One example of such prior art is U.S. Pat. No. 4,276,883 granted July 7, 1981 to McDonald et al. This patent discloses a pacemaker having a number of programmable features including the pacing rate and pulse width. Information concerning these operating parameters is stored in digital form in the pacemaker's memory. After implantation it is desirable to read out these memory locations for diagnostic purposes. Additional information which is useful for diagnostic purposes, such a lead impedance, battery voltage, and the patient's intracardiac electrogram are inherently analog in nature and not directly compatible with the other digital information within the pacemaker. Consequently, conventional digital modems have not been applicable to pacemaker telemetry systems since their use would require the periodic conversion of the aforementioned analog data to a numerical value prior to transmission.

In contrast, the pulse interval telemetry system of the present invention is capable of transmitting analog data without conversion to a numerical value, and is capable of sequentially transmitting both digital and analog data. This data is individually and serially transmitted in either an analog or digital format to a remote receiver.

BRIEF DESCRIPTION OF THE DRAWINGS

FIG. 1 is a block diagram of the function elements of the system for encoding and transmitting information from the implanted medical device.

FIG. 2 is a truth table showing the relationship between the encoding scheme and the corresponding states of the various current sources of the system;

FIG. 3 is a waveform diagram showing the analog and digital data format; and

FIG. 4 is a schematic diagram showing the VFO, and current sources in a form suitable for implementation in a bipolar integrated circuit.

DESCRIPTION OF THE PREFERRED EMBODIMENT

General

As previously described, the pulse interval modulation telemetry system is used to transmit analog and digital information from the implanted medical device to a remote receiver. In the context of a pacemaker application the analog information may include battery voltage, lead impedance, or the patient's intracardiac electrogram. Similarly, typical digital data may include programmed pulse width and rate settings as well as identification information. An example of a pacemaker suitable for use as a source of digital information is taught by the previously mentioned U.S. Pat. No. 4,276,883 granted July 7, 1981, to McDonald et al. This application discloses a digitally implemented pacemaker having memory for storing digitally programmed information shown in FIG. 6H of the referenced patent. This information is stored in a parallel format as a sequence of binary digits.

A suitable source for analog information such as the patient's intracardiac electrogram may be found in U.S. Pat. No. 4,266,551 granted May 12, 1981 to Stein et al. The circuitry disclosed in this patent may be used to provide a source of intracardiac analog information to the telemetry system of the present invention.

As shown schematically in FIG. 1 the heart 10 has an indwelling catheter 11 for sensing cardiac depolarizations and for stimulating cardiac tissue. Pacer logic receives signals via sense amplifier 34 and delivers stimulating pulses by way of output amplifier 33. The pacer logic 12 shown operates under the control of parameter data stored in memory 15. The memory 15 contains the parameter data in parallel form which is serialized for data transmission by shift register 16 which forms a portion of the telemetry system.

In operation, the transmission of data is remotely initiated by the closure of a magnetically actuated reed switch within the pacemaker in the well-known manner. Digital data is then transmitted twice to a remote receiver where it is decoded and checked for errors. The digital data transmission is followed by the transmission of analog data in an analog format. The telemetry system is disabled by removing the magnet from the pacemaker site which opens the reed switch and disables the telemetry circuitry.

Additionally, the telemetry circuitry of the present invention includes a receiver blanking circuit which permits the transmission of analog or digital data to be interrupted by the remote programmer thus truncating the transmission of telemetry information so that the pacemaker may receive higher priority programming information from the remote programmer. This function is achieved by digital circuitry which detects the presence of a long duration burst of RF energy from the remote programmer which is received by the pacemaker and which is decoded to turn off the telemetry transmission systems and to prepare the digital circuitry for the reception of programming information from the remote programmer.

Oscillators

Referring to FIG. 1 the radio frequency carrier signal is developed by a radio frequency oscillator tank in FIG. 1. The tank circuit 14 is energized at periodic intervals determined by a variable frequency oscillator (VFO) 12. Radio frequency energy from the resonant tank circuit 14 is coupled to antenna 16 which radiates this energy to a remote receiver (not shown).

The repetition rate of the variable frequency oscillator is set by a number of cooperating current sources which establish a net charging rate at the input node 18 of the VFO 12. When operating in the digital mode for the transmission of digital information the current sources establish a first characteristic charging rate for encoding a logic one and a second characteristic charging rate for encoding a logic zero.

As shown in FIG. 1, three cooperating current sources 26, 28 and 30, are energized by control logic, operating switches 20, 22, 24. When each of these current sources is turned on, a characteristic current I, 0.5 I or 0.25 I is supplied to the capacitor 32 which establishes a voltage at node 18. When the voltage on capacitor 32 reaches a trip level, the VFO output will change state initiating a burst of RF energy from the tank circuit 14. Consequently, the time period between successive bursts of radio frequency energy will be determined by the number of current sources which are on. The truth table FIG. 2 indicates the relationship between the encoding scheme of the present invention and the states of the various current sources. As indicated in the diagram, the logic "one" signal is encoded by energizing current source 30 by closing switch 24, which provides a constant current charging rate to capacitor 32 of magnitude I. In the preferred embodiment this characteristic charging rate results in a pulse interval of 1,000 microseconds. Similarly, a logic "zero" is encoded by energizing the two current sources 28 and 30 resulting in a net charging current of 1.5 I which results in a shorter, 667 microsecond pulse interval. This is accomplished by closure of switches 22 and 24.

In the analog mode, an alternate pair of current sources 26 and 30 are energized to provide a nominal charging rate corresponding to an 800 microsecond pulse interval. A suitable analog such as the intracardiac electrogram derived from the pacemaker lead system is used to modulate one of the current sources 26 to vary the nominal charging rate in a positive or negative direction. This current modulation results in a varying pulse interval which corresponds to the amplitude variations of the intracardiac signal.

As shown in FIG. 3, digital data corresponding to a serial stream of logic one and logic zeroes is encoded by time periods between shorter and longer time period between bursts of radio frequency energy. It is important to note that the longer interval of 1,000 microseconds is not an even multiple of the shorter time period of 667 microseconds used to encode a logic zero. This scheme results in a lower error rate than systems wherein the logic zero and logic one are related as integer multiples. As shown in the lower analog traces of FIG. 3, a nominal time period of 800 microseconds corresponds to the zero level of the analog signal to be transmitted. Positive and negative excursions indicated by the phantom wave traces are used to encode the minimum and maximum excursions about the nominal value.

Although the telemetry system has been described with reference to only a single analog channel, it should be clear that a time division multiplexing scheme could be employed to simultaneously transmit more than one channel of analog data 36 as shown in FIG. 1. The sequential transfer of more than one analog channel is desirable for use with dual chamber pacemakers whose performance depends upon intrinsic atrial and ventricular electrograms. One possible scheme for achieving this time division multiplexing is using a multiplexer 35, shown in FIG. 2 wherein an additional analog channel, labeled "Analog B", is encoded by activating both current sources 28 and 26.

In a similar fashion, other analog signal sources 36 such as lead impedance or battery voltage could be suitably buffered and applied to variable current source 26 to establish a charging rate proportional to the analog signal.

Control Logic and Current Sources

The block diagram of FIG. 1 shows the two constant current sources 28 and 30 and one variable current sources 26 energized by suitable switching means interfaced to control logic 38. In practice, the switching and current sourcing function may be combined by the use of bipolar transistors which have a characteristic collector-emitter current which corresponds to the magnitude of injected base current. One suitable bipolar implementation for these current sources is shown in FIG. 4. Referring now to FIG. 4 the operation of this circuit is initiated by a reed switch closure connecting node 100 to the positive supply voltage. This connection supplies bias current to transistors 102, 104, 106, 108 which, in turn, supply bias current to transistors 110, 111, 112, 113, 114, 116, 118, 120 and to transistors 122, 124 and 126. Input node 99 interfaces the current source system with the sources of digital and analog data. This node 99 is connected to the positive supply voltage through a tri-state buffer when a logic "zero" is to be transmitted. The node 99 is connected to ground through the tri-state buffer for the transmission of "analog" information. The node 99 is disconnected and is floating when the tri-state buffer is in the high impedance configuration for the transmission of a logic "one".

For the transmission of a logic "one", transistor 118 is off and transistor 120 supplies approximately 225 nanoamps of current to the junction of the base of transistor 128 and the VFO capacitor 32. Assuming that capacitor 32 is near ground potential, then transistors 129, 130, 132, 134 and 136 are off. The voltage on capacitor 32 increases because of the charging current supplied by transistor 120 until the base of transistors 128 and 129 are equal. This allows current flow in transistors 129 and 138. When the collector-emitter current of transistor 129 exceeds the current flow through transistor 138, excess current flows into transistor 134, which turns it on. This, in turn, turns on transistor 136 which sinks current through the tank circuit 14 and causes the emission of a pulse of radio frequency. The circuit formed by transistors 130, and 134 form a latch arrangement which will not change state until the capacitor 32 discharges to approximately 0.5 volt whereupon these transistors shut off. The discharge of capacitor 32 takes approximately 2 microseconds and determines the time transistor 136 is on, which determines the width of the pulse applied to the tank circuit. When capacitor 32 is discharged, transistor 129 is off and transistor 128 is on which permits the cycle to begin again.

When a logic "one" is applied to input node 99, transistor 118 is activated which adds additional current to the VFO input node 18, shortening the time required to reach the trip level of the VFO circuit, thus shortening the pulse interval time to approximately 667 microseconds.

When input node 99 is grounded through the operation control logic, the analog transmission mode is enabled and an analog voltage signal applied to the base of transistor 142 is converted to a proportional charging current by transistors 142, 144, 146, 148, 140. As the analog voltage varies, the current of transistor 148 is modulated and the result of pulse interval is shifted with respect to the nominal 800 microsecond pulse interval.

Although the current sources and VFO have been shown implemented in bipolar technology, it should be appreciated tht equivalent structures exist in other technologies including metal oxide semiconductor technologies, and that other modifications may be made without departing from the scope of the invention.

What is claimed is:

1. In a transmitter for transmitting signals from an implantable medical device which are representative of either analog or digital values comprising a signal controlled variable frequency oscillator means having a control terminal, signal application means for selectively presenting information signals representative of said digital and analog values to said control terminal to vary the frequency of said oscillator means in response thereto relative to a nominal output frequency of said oscillator means that exists when said information signals are not being supplied, a tank circuit and antenna means having a predetermined ringing frequency of oscillation when pulsed with energy, and drive circuit means coupled to said oscillator means and to said tank circuit and antenna means for supplying pulses of energy to said tank circuit and antenna means at a rate that is proportional to the output frequency of said oscillator means whereupon said pulses are radiated from said tank circuit and antenna means as damped ringing signals; the improvement wherein said signal applicatiion means comprises a selectively activated digital signal means which in a first state provides a first digital current level signal to said control terminal that is representative of a digital "one" and in second state provides a second digital current level signal to said control terminal that is representative of a digital "zero", first and second sources of analog information, a selectively actuated analog signal means which, when selected provides either a first analog current level signal in accordance with the information content of said first source or a second analog current level signal in accordance with the information content of said second source, means for selecting either said first or said second analog current level signal and means for selectively adding said first digital current level signal to said first analog current level signal and for selectively adding said second digital current level signal to said second analog current level signal and means for providing said added current level signals to said control terminal.

* * * * *